United States Patent
Würthner et al.

(10) Patent No.: US 6,806,368 B2
(45) Date of Patent: Oct. 19, 2004

(54) LIQUID CRYSTALLINE 3,4:9,10-PERYLENETETACARBOCYLIC ACID DIIMIDES

(75) Inventors: Frank Würthner, Ulm (DE); Christoph Thalacker, Ulm (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/344,368

(22) PCT Filed: Jul. 24, 2001

(86) PCT No.: PCT/EP01/08524

§ 371 (c)(1),
(2), (4) Date: Feb. 11, 2003

(87) PCT Pub. No.: WO02/14318

PCT Pub. Date: Feb. 21, 2002

(65) Prior Publication Data

US 2003/0181721 A1 Sep. 25, 2003

(30) Foreign Application Priority Data

Aug. 11, 2000 (DE) .......................... 100 39 232

(51) Int. Cl.[7] .................. C07D 471/06; C09K 19/34; C09B 5/62; C07B 67/04; C03G 5/07
(52) U.S. Cl. .................. 546/37; 252/299.1; 252/299.61; 252/301.26; 430/78; 430/58.6; 106/498
(58) Field of Search .................. 546/37; 252/299.1, 252/299.61, 301.26; 430/78, 58.6; 106/498

(56) References Cited

U.S. PATENT DOCUMENTS

| | | | |
|---|---|---|---|
| 3,294,778 A | | 12/1966 | Randall et al. |
| 3,554,776 A | * | 1/1971 | Gerson ................. 106/494 |
| 4,378,302 A | | 3/1983 | Aftergut et al. |
| 5,151,516 A | | 9/1992 | Beck et al. |
| 5,677,417 A | | 10/1997 | Muellen et al. |
| 6,143,905 A | | 11/2000 | Boehm et al. |

FOREIGN PATENT DOCUMENTS

| | | |
|---|---|---|
| DE | 3016764 | * 11/1981 |
| DE | 31 10 955 | 9/1982 |
| DE | 196 20 746 | 11/1997 |

OTHER PUBLICATIONS

F. Wuerthner et al.: "Fluorescent J–type aggregates and thermotropic columnar mesophases of perylene bisimide dyes" Chem. Eur. J., vol. 7, No. 10, pp. 2245–2253 May 10, 2001.
R.A. Cormier et al.: "Synthesis and characterization of liquid crystalline perylene diimides" Chem. Mater., vol. 10, pp. 1309–1319 1998.
Ulrike Rohr et al.: "Fluessigkristalline coronenderivate mit aussergewoehnlichen fluoreszenziegenschaften" Angew. Chem., vol. 110, No. 10, pp. 1463–1467 1998.

* cited by examiner

Primary Examiner—Evelyn Mei Huang
(74) Attorney, Agent, or Firm—Oblon, Spivak, McClelland, Maier & Neustadt, P.C.

(57) ABSTRACT

Perylene-3,4:9,10-tetracarboxylic diimides of the general formula I

I

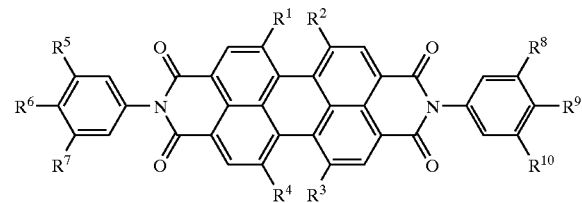

where
- $R^1$, $R^2$, $R^3$ and $R^4$ are independently hydrogen, chlorine, bromine or substituted or unsubstituted aryloxy, arylthio, arylamino, hetaryloxy or hetarylthio;
- $R^5$, $R^6$, $R^7$, $R^8$, $R^9$ and $R^{10}$ are independently hydrogen or long-chain alkyl, alkoxy or alkylthio whose carbon chain may in each case contain up to four double bonds, with the proviso that at least four of these radicals are not hydrogen are prepared and used as liquid-crystalline materials for electronic, optoelectronic and photonic applications, for coloration of macromolecular organic and of inorganic materials, as fluorescent dyes and as laser dyes and also as organic materials for solar collectors and electroluminescence applications.

14 Claims, No Drawings

LIQUID CRYSTALLINE 3,4:9,10-PERYLENETETACARBOCYLIC ACID DIIMIDES

CROSS-REFERENCE TO RELATED APPLICATIONS

This application is a 371 of PCT/EP01/08524 filed Jul. 24, 2001 which is based on German priority application Serial No. 10039232.6 filed Aug. 11, 2000.

BACKGROUND OF THE INVENTION

1. Field of the Invention

The present invention relates to novel perylene-3,4:9,10-tetracarboxylic diimides (hereinafter referred to as perylimides for short) of the general formula I

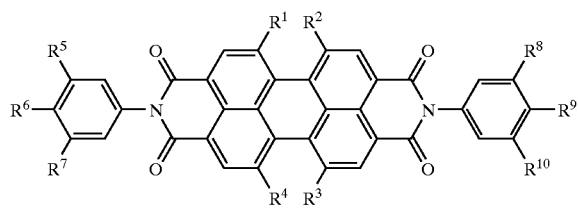

where $R^1$, $R^2$, $R^3$ and $R^4$ are independently hydrogen, chlorine, bromine or substituted or unsubstituted aryloxy, arylthio, arylamino, hetaryloxy or hetarylthio;

$R^5$, $R^6$, $R^7$, $R^8$, $R^9$ and $R^{10}$ are independently hydrogen or long-chain alkyl, alkoxy or alkylthio whose carbon chain may in each case contain up to four double bonds, with the proviso that at least four of these radicals are not hydrogen.

The invention also relates to the preparation of these perylimides and to their use as liquid-crystalline materials for electronic, optoelectronic and photonic applications, for coloration of macromolecular organic and of inorganic materials, as fluorescent dyes and as laser dyes and also as organic materials for solar collectors and electroluminescence applications.

2. Description of the Background

There are a multiplicity of technological applications, for example charge transport material applications, where the materials used have to have not only suitable molecular properties such as color and emission but also a supramolecular order, which is customarily determined by the relationship of the molecules in the crystal.

Particularly interesting arrangements of functional molecules are obtained in liquid-crystalline phases, which have substantial advantages in use over pigmentary solids. For instance, the mobility of the molecules in the liquid-crystalline phase makes it possible to prepare films of uniform thickness and of a macroscopic order induced by the substrate. When low viscosities are desired for the production process, films may also be prepared by raising the temperature above the melting point. On the other hand, liquid-crystalline orders which are stable over wide temperature ranges are also obtainable by attaching thermally or photochemically crosslinkable groups.

Perylimides have hitherto formed the basis for the following liquid-crystalline compounds:

Chem. Mater. 10, 1309–1319 (1998) describes perylimides which are derivatized at the imide nitrogen atoms with oligoethyleneoxy substituents as mesogenic groups. However, these groups tend to absorb atmospheric humidity, so that thin films of the liquid-crystalline phase in particular are not morphologically stable.

Angew. Chem. 110, 1463–1467 (1998) concerns liquid-crystalline coronenediimides which, however, form columnar liquid-crystalline phases only at above 150° C. and are preparable from perylene derivatives only by means of inconvenient processes.

EP-A-422 535 describes liquid-crystalline polymers which are partly functionalized with perylimide units in the side chains; that is, are not intrinsically liquid-crystalline low molecular weight dyes.

WO-A-97/22607 and 94/25504 disclose perylimides which are 1,7-disubstituted or 1,6,7,12-tetrasubstituted in the perylene structure, but which differ from the claimed perylimides of the formula I not least by the substitution on the imide nitrogen atoms and are not liquid crystalline.

SUMMARY OF THE INVENTION

It is an object of the present invention to provide further liquid-crystalline dyes having advantageous application properties.

We have found that this object is achieved by the perylimides of the formula I defined at the beginning.

Preferred perylimides of the formula I are disclosed in the subclaims.

The invention also provides a process for preparing these perylimides, which comprises reacting a perylene-3,4:9,10-tetracarboxylic dianhydride of the general formula II

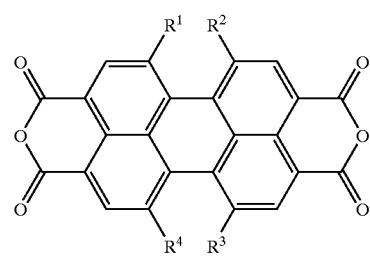

with identical or different primary amines of the general formulae III

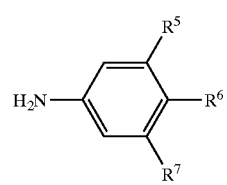

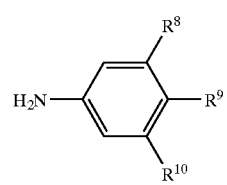

in the presence of a polar aprotic solvent and of an imidation catalyst.

The invention further provides a process for preparing perylene-3,4:9,10-tetracarboxylic diimides of the general formula Ia

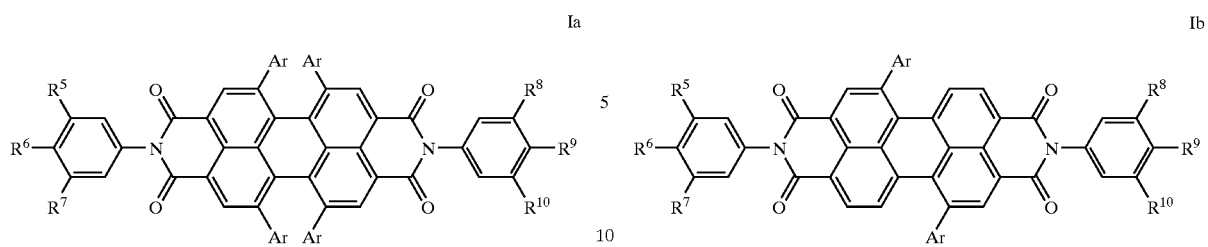

Ia where Ar is substituted or unsubstituted aryloxy, arylthio, hetaryloxy or hetarylthio, which comprises reacting 1,6,7,12-tetrachloroperylene-3,4:9,10-tetracarboxylic dianhydride (IIa) with identical or different primary amines of the general formulae III

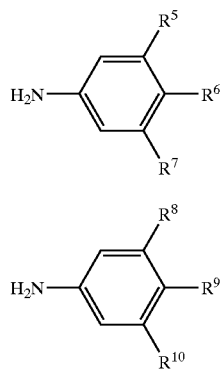

IIIa

IIIb in the presence of a polar aprotic solvent and of an imidation catalyst and reacting the resultant 1,6,7,12-tetrachloroperylene-3,4:9,10-tetracarboxylic diimides of the general formula I'

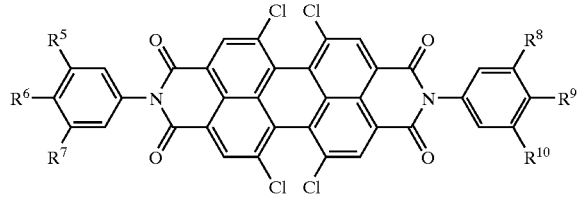

I' with an aromatic alcohol or thioalcohol of the general formula IV

    IV in the presence of an inert aprotic solvent and of a non-nucleophilic or only minimally nucleophilic base.

The invention further provides a process for preparing perylene-3,4:9,10-tetracarboxylic diimides of the general formula Ib where Ar is substituted or unsubstituted aryloxy, arylthio, hetaryloxy or hetarylthio, which comprises reacting 1,7-dibromoperylene-3,4:9,10-tetracarboxylic dianhydride (IIb) with identical or different primary amines of the general formulae III

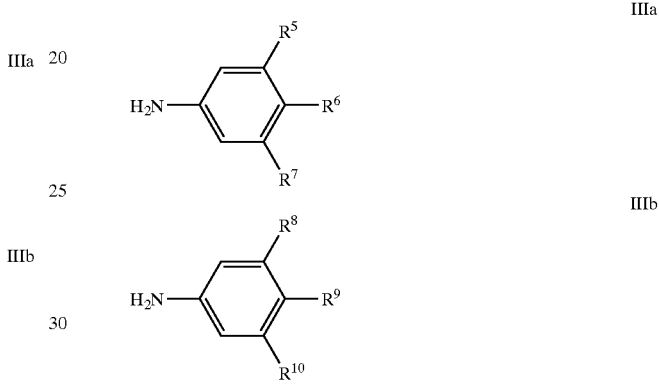

IIIa

IIIb in the presence of a polar aprotic solvent and of an imidation catalyst and reacting the resultant 1,7-dibromoperylene-3,4:9,10-tetracarboxylic diimides of the general formula I"

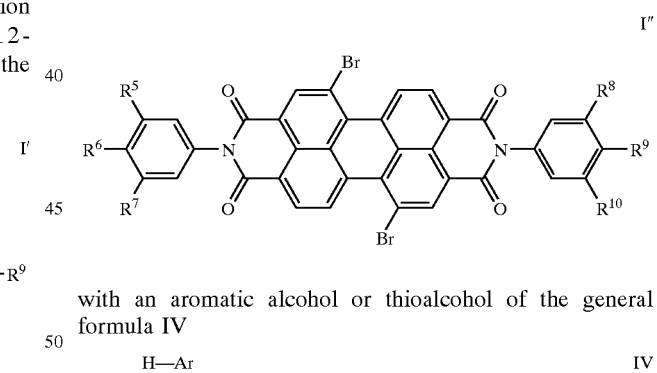

I"

with an aromatic alcohol or thioalcohol of the general formula IV

    IV in the presence of an inert aprotic solvent and of a non-nucleophilic or only minimally nucleophilic base.

The invention further provides for the use of the perylimides of the formula I as liquid-crystalline materials in electronic, optoelectronic or photonic applications, for coloration of macromolecular organic and of inorganic materials, as fluorescent dyes and as laser dyes and also as organic materials for solar collectors and electroluminescence applications.

DETAILED DESCRIPTION OF THE PREFERRED EMBODIMENTS

The variables in the formula I will now be more particularly described.

Examples of nonhydrogen radicals $R^1$ to $R^4$ are chlorine, bromine, phenoxy, phenylthio, phenylamino, 2-naphthyloxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio, of which chlorine and bromine are preferred and phenoxy is particularly preferred.

When the perylene structure is to be substituted, preferably all or just two (especially 1,7-substitution) of the radicals $R^1$ to $R^4$ are identical ones of the abovementioned radicals. Aryl and hetaryl may each bear up to three, preferably one or two, substituents.

Examples of these substituents are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, tert-octyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above designations isooctyl, isononyl, isodecyl and isotridecyl are trivial names derived from the alcohols obtained in the oxo process), of which $C_1$–$C_8$-alkyl radicals and especially tert-butyl are preferred;

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-methylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

methylcarboxymethyl, ethylcarboxymethyl, propylcarboxymethyl, butylcarboxymethyl, pentylcarboxymethyl, hexylcarboxymethyl, methyl-2-carboxyethyl, ethyl-2-carboxyethyl, propyl-2-carboxyethyl, butyl-2-carboxyethyl, pentyl-2-carboxyethyl, hexyl-2-carboxyethyl, methyl-3-carboxypropyl, ethyl-3-carboxypropyl, propyl-3-carboxypropyl, butyl-3-carboxypropyl, pentyl-3-carboxy-propyl, hexyl-3-carboxypropyl, methyl-4-carboxybutyl, methyl-5-carboxypentyl, methyl-6-carboxyhexyl, methyl-8-carboxyoctyl, methyl-10-carboxydecyl, methyl-12-carboxydedecyl and methyl-14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

methylsulfomethyl, ethylsulfomethyl, propylsulfomethyl, butylsulfomethyl, pentylsulfomethyl, hexylsulfomethyl, methyl-2-sulfoethyl, ethyl-2-sulfoethyl, propyl-2-sulfoethyl, butyl-2-sulfoethyl, pentyl-2-sulfoethyl, hexyl-2-sulfoethyl, methyl-3-sulfopropyl, ethyl-3-sulfopropyl, propyl-3-sulfopropyl, butyl-3-sulfopropyl, pentyl-3-sulfopropyl, hexyl-3-sulfopropyl, methyl-4-sulfobutyl, methyl-5-sulfopentyl, methyl-6-sulfohexyl, methyl-8-sulfooctyl, methyl-10-sulfodecyl, methyl-12-sulfododecyl and methyl-14-sulfotetradecyl;

2-hydroxyethyl, 2- and 3-hydroxypropyl, 1-hydroxyprop-2-yl, 2- and 4-hydroxybutyl, 1-hydroxybut-2-yl and 8-hydroxy-4-oxaoctyl;

2-cyanoethyl, 3-cyanopropyl, 2-methyl-3-ethyl-3-cyanopropyl, 7-cyano-7-ethylheptyl and 4-methyl-7-methyl-7-cyanoheptyl;

methoxy, ethoxy, propoxy, isopropoxy, butoxy, isobutoxy, sec.-butoxy, tert-butoxy, pentyloxy, isopentyloxy, neopentyloxy, tert-pentyloxy, hexyloxy and 2-methylpentyloxy;

cyclopentyl, cyclohexyl, cycloheptyl, cyclooctyl, morpholinyl, pyrrolidinyl and piperidyl.

Examples of particularly preferred substituted aromatic radicals $R^1$ to $R^4$ are 4- and 3-tert-butylphenoxy, 4-cyclohexylphenoxy, 4-propoxyphenoxy, 4-butoxyphenoxy, 4-hexyloxyphenoxy and 1,1,3,3-tetramethylbutylphenoxy.

At least four of the radicals $R^5$ to $R^{10}$ which substitute into the phenyl radicals on the imide nitrogen atoms are not hydrogen, and preferably two phenyl radicals each bear two of the nonhydrogen substituents. Both 3,5- and 3,4-disubstitution are possible. Preferably, however, all radicals $R^5$ to $R^{10}$ are not hydrogen. And they may be identical or different. Preferably, however, at least the radicals sitting on any one phenyl radical are identical. Particular preference is given to perylimides of the formula I where the two phenyl radicals bear the same substituents.

The alkyl chains of the radicals $R^5$ to $R^{10}$ may be linear or branched and generally have 8 to 20, preferably 10 to 14, carbon atoms.

In addition to the alkyl radicals already mentioned above, the following alkoxy and alkylthio radicals may be mentioned as suitable for the radicals $R^5$ to $R^{10}$ by way of example:

octyloxy, 2-ethylhexyloxy, isooctyloxy, nonyloxy, isononyloxy, decyloxy, isodecyloxy, undecyloxy, dodecyloxy, tridecyloxy, tetradecyloxy, pentadecyloxy, hexadecyloxy, heptadecyloxy, octadecyloxy, nonadecyloxy and eicosyloxy;

octylthio, 2-ethylhexylthio, isooctylthio, nonylthio, isononylthio, decylthio, isodecylthio, undecylthio, dodecylthio, tridecylthio, tetradecylthio, pentadecylthio, hexadecylthio, heptadecylthio, octadecylthio, nonadecylthio and eicosylthio.

In addition, the alkyl chains of the radicals $R^5$ to $R^{10}$ may contain one to four, especially three, double bonds. Of these unsaturated radicals, especially those radicals are suitable that are derived from naturally occurring terpene hydrocarbons and terpene alcohols and from the alcohols of unsaturated fatty acids. Particularly suitable alkenyloxy radicals are formed for example by geraniol, nerol, linalool and citronellol and also the alcohols of oleic acid, linoleic acid and linolenic acid.

Examples of particularly preferred phenyl substituents on the imide nitrogen atoms are 3,4,5-tridodecyloxyphenyl, 3,4,5-tridecyloxyphenyl, 3,5- and 3,4-didodecyloxyphenyl.

The inventive perylimides of the formula I are advantageously preparable by the similarly inventive process by reacting the substituted or unsubstituted perylene-3,4:9,10-tetracarboxylic dianhydrides of the formula II with identical or different primary amines of the formulae III in the presence of a polar aprotic solvent and of an imidation catalyst.

Useful polar aprotic solvents include in particular aprotic nitrogen heterocycles, such as pyridine, pyrimidine, imidazole, quinoline, isoquinoline, quinaldine, N-methylpiperidine, N-methylpiperidone and N-methylpyrrolidone, carboxamides, such as dimethylformamide and dimethylacetamide, and tetraalkylureas, such as tetramethylurea, of which quinoline is particularly preferred.

The amount of solvent is not critical per se. From 5 to 120 g of solvent may be used per g of perylene-3,4:9,10-tetracarboxylic dianhydride (II).

Useful imidation catalysts include in particular Lewis-acidic salts of organic and inorganic acids with metals such as zinc, iron, copper and magnesium and also the oxides of these metals, for example zinc acetate, zinc propionate, zinc oxide, iron(II) acetate, iron(III) chloride, iron(II) sulfate, copper(II) acetate, copper(II) oxide and magnesium oxide, of which zinc acetate is particularly preferred. It will be appreciated that mixtures of the catalysts mentioned may also be used. Preferred amounts of metal catalyst range from about 20 to 100 mol %, based on (II).

It is also possible to use the acids themselves, for example organic acids, especially $C_1$–$C_3$-carboxylic acids such as formic acid, acetic acid and propionic acid, and inorganic acids such as phosphoric acid, each preferably in very concentrated form, as imidation catalysts. The acids here also act as solvents or as a cosolvent and are therefore customarily used in excess.

The molar ratio of primary amine (III) to a perylene-3,4:9,10-tetracarboxylic dianhydride (II) is customarily in the range from about 2:1 to 4:1, preferably in the range from about 2.2:1 to 3:1.

The reaction temperature is generally in the range from 60 to 250° C., preferably in the range from 100 to 230° C., particularly preferably in the range from 160 to 200° C.

It is advisable to conduct the reaction under a protective gas atmosphere (preferably argon or else nitrogen).

It is generally not necessary to employ superatmospheric pressure in the case of this inventive process.

The reaction customarily ends in from 1 to 4 h.

An advantageous procedure is as follows:

Perylene-3,4:9,10-tetracarboxylic dianhydride (II), solvent and catalyst are initially charged, the amine (III) is added at room temperature with stirring, the apparatus is purged with argon for about 10 min, and the stirred mixture is heated to the reaction temperature and maintained at that temperature for from about 2 to 3 h. After cooling to room temperature, the reaction product is filtered off and washed with water and then with an aliphatic alcohol such as methanol.

The product may be purified by recrystallization (e.g., dissolving in an organic solvent such as dichloromethane and reprecipitating with an aliphatic alcohol such as methanol) or by column chromatography (e.g., silica gel/dichloromethane).

When the perylene-3,4:9,10-tetracarboxylic dianhydride (II) is to be reacted with two different amines (IIIa) and (IIIb), the reaction is advantageously carried out in stages, by using first the amine (IIIa) in an amount of from about 0.8 to 1 mol per mole of (II) and, after the formation of the monoimide has ended, the amine (IIIb) in an amount of from about 1 to 2 mol per mole of (II) to form the diimide (cf. Adv. Mater. 11, 754–758 (1999)).

This inventive process advantageously provides the perylimides of the formula I in high purity (generally $\geq 95\%$) and good yield (generally in the range from 60 to 95%).

The perylene-3,4:9,10-tetracarboxylic dianhydrides (II) used as starting materials for this inventive preparative process are known per se or are preparable by known methods starting from 1,6,7,12-tetrachloroperylene-3,4:9,10-tetracarboxylic dianhydride (IIa) or 1,7-dibromoperylene-3,4:9,10-tetracarboxylic dianhydride (IIb) (cf. WO-A-97/22607 and EP-A-227 980).

A further way to prepare the (het)aryloxy- and (het)arylthio-substituted perylimides of the formulae Ia and Ib comprises as per the further inventive processes a first step of reacting 1,6,7,12-tetrachloroperylene-3,4:9,10-tetracarboxylic dianhydride (IIa) or 1,7-dibromoperylene-3,4:9,10-tetracarboxylic dianhydride (IIb) with identical or different primary amines of the formulae III in the presence of a polar aprotic solvent and of an imidation catalyst and further reacting the resultant 1,6,7,12-tetrachloroperylene-3,4:9,10-tetracarboxylic diimides of the formula I' or 1,7-dibromoperylene-3,4:9,10-tetracarboxylic diimides of the formula I'' in a second step with an aromatic (thio)alcohol of the formula IV in the presence of an inert aprotic solvent and of a non-nucleophilic or only minimally nucleophilic base.

The first step of this inventive preparative process may be carried out similarly to the above-described process.

The second step of this preparative process, which may be carried out as described in WO-A-97/22607, usefully employs as the inert aprotic solvent in particular nitrogen heterocycles such as pyridine, pyrimidine, quinoline, isoquinoline, quinaldine and especially N-methylpyrrolidone as inert aprotic reaction medium.

The amount of solvent is not critical per se. Typically from 10 to 50 g, preferably from 25 to 35 g, of solvent are used per g of perylimide of the formula I' or I''.

Preferred bases include alkali metal hydroxides, e.g., sodium hydroxide and potassium hydroxide, and especially alkali metal carbonates, e.g., sodium carbonate and potassium carbonate.

Generally from 2 to 3, preferably from 2.2 to 2.5, mol equivalents of base are used per mole of perylimide of the formula I' or I''.

The molar ratio of aromatic (thio)alcohol (IV) to perylimide of the formula I' or I'' is generally in the range from 2:1 to 3:1, preferably in the range from 2.0:1 to 2.2:1.

The reaction temperature is customarily in the range from 60 to 180° C., especially in the range from 80 to 140° C.

It is again advisable to employ a protective gas atmosphere.

The reaction customarily ends in from 1 to 5 h, especially in from 1 to 2 h.

An advantageous procedure for this second step is as follows:

A stirred suspension of perylimide (I') or (I"), (thio) alcohol (IV) and base in the solvent is initially charged and heated to the reaction temperature under a protective gas over from 1 to 2 h. After cooling to room temperature, the reaction mixture is discharged into about 3 times the volume of a dilute inorganic acid, for example 5–10% by weight hydrochloric acid, the precipitated reaction product is filtered off, washed neutral with water and dried under reduced pressure.

Generally the perylimides of the formula Ia or Ib thus obtained are already ≧95% pure, so that there is no need for further purification. In the event that additional purification is desired, however, this additional purification may be carried out as in the case of the further preparative process already described.

The inventive perylimides of the formula I form stable liquid-crystalline phases and so are very useful for a multiplicity of applications, especially for electronic, optoelectronic and photonic applications, for example as charge transport materials in luminescent diodes and photovoltaic diodes, photoconductors and transistors. They are also useful as fluorescent dyes for coloration of macromolecular organic materials (e.g., polyolefins) and of inorganic materials and as laser dyes. They are useful not least as organic materials for solar collectors and for electroluminescence applications, for example in displays.

EXAMPLES

A) Preparation of Inventive Perylimides

Example 1

N,N'-Di(3,4,5-tridodecyloxyphenyl)perylene-3,4:9,10-tetracarboxylic diimide

A mixture of 0.12 g (0.3 mmol) of perylene-3,4:9,10-tetracarboxylic dianhydride, 0.58 g (0.9 mmol) of 3,4,5-tridodecyloxyaniline, 0.04 g (0.2 mmol) of zinc acetate and 12 ml of quinoline was heated at 180° C. under argon for 3 h.

After cooling to room temperature, the reaction mixture was poured into 100 ml of 1 N hydrochloric acid with stirring. The red precipitate obtained was filtered off with suction and washed with water and then with methanol. The product was then purified by dissolving in dichloromethane and precipitating with methanol and dried at 70° C. under medium vacuum.

This provided 0.44 g of a 99% pure product, which corresponds to a yield of 89%.

Analytical Data

Elemental analysis for $C_{108}H_{162}N_2O_{10}$ (1648.5) (% by weight calc./obs.):

C: 78.69/78.50; H: 9.91/9.81; N: 1.70/1.62;

1H NMR (200 MHz, $CDCl_3$, 25° C., TMS): δ=8.54 (d, 3J (H,H)=7.8 Hz, 4H; H2,5,8,11), 8.21 (d, 3J (H, H)=7.8 Hz, 4H; H1,6,7,12), 6.63 (s, 4H; ArH), 4.03 (t, 4H; $OCH_2$), 3.86 (t, 8H; $OCH_2$), 1.76 (m, 12H), 1.6–1.2 (m, 108H), 0.85 (m, 18H) ppm;

UV/Vis ($CH_2Cl_2$): $\lambda_{max}$ (ε) 527 (89 600), 490 (59 500), 459 nm (22 300 $mol^{-1}$ $dm^3$ $cm^{-1}$).

Example 2

N,N'-Di(3,4,5-tridodecyloxyphenyl)-1,7-di(4-tert-butylphenoxy)-perylene-3,4:9,10-tetracarboxylic diimide Example 1 was repeated, except that 0.34 g (0.5 mmol) of 1,7-di(4-tert-butylphenoxy)perylene-3,4:9,10-tetracarboxylic dianhydride and 0.97 g (1.5 mmol) of 3,4,5-tridodecyloxyaniline and 0.05 g (0.3 mmol) of zinc acetate were used.

The dark red product was purified by column chromatography over silica gel using dichloromethane.

This provided 0.58 g of a 99% pure product, which corresponds to a yield of 60%.

Analytical Data

Elemental analysis for $C_{128}H_{186}N_2O_{12}$ (1944.6) (% by weight calc./obs.):

C: 79.05/79.00; H: 9.64/9.77; N: 1.44/1.49;

1H NMR (200 MHz, $CDCl_3$, 25° C., TMS): δ=9.52 (d, 3J (H,H)=8.4 Hz, 2H; H6,12), 8.53 (d, 3J (H,H)=8.4 Hz, 2H; H5,11), 8.27 (s, 2H; H2,8), 7.47 (d, 3J (H,H)=8.7 Hz, 4H; H3'), 7.10 (d, 3J (H,H)=8.7 Hz, 4H; H2'), 6.52 (s, 4H; ArH), 4.00 (t, 4H; $OCH_2$), 3.83 (t, 8H; $OCH_2$), 1.74 (m, 12H), 1.6–1.2 (m, 108H), 1.36 (s, 18H; tert-Bu), 0.87 (m, 18H) ppm;

UV/Vis ($CH_2Cl_2$): $\lambda_{max}$ (ε)=546 (57 500), 511 (39 600), 402 nm (11 600 $mol^{-1}$ $dm^3$ $cm^{-1}$).

Example 3

N,N'-Di(3,4,5-tridodecyloxyphenyl)-1,6,7,12-tetraphenoxyperylene-3,4:9,10-tetracarboxylic diimide Example 1 was repeated, except that 0.19 g (0.25 mmol) of 1,6,7,12-tetraphenoxyperylene-3,4:9,10-tetracarboxylic dianhydride, 0.48 g (0.75 mmol) of 3,4,5-tridodecyloxyaniline, 0.04 g (0.2 mmol) of zinc acetate and 10 ml of quinoline were used.

The purple precipitate was purified similarly to Example 2.

This provided 0.35 g of a 99% pure product, which corresponds to a yield of 69%.

Analytical Data

Elemental analysis for $C_{132}H_{178}N_2O_{14}$ (2016.9) (% by weight calc./obs.):

C: 78.61/78.40; H: 8.90/9.02; N: 1.39/1.40;

1H NMR (400 MHz, $CDCl_3$, 25° C., TMS): δ=8.22 (s, 4H; H2,5,8,11), 7.25 (t, 3J (H,H)=8.0 Hz, 8H; H3'), 7.10 (t, 3J (H,H)=7.4 Hz, 4H; H4'), 6.95 (d, 3J (H,H)=8.1 Hz, 8H; H2'), 6.41 (s, 4H; ArH), 3.99 (t, 4H; $OCH_2$), 3.89 (t, 8H; $OCH_2$), 1.76 (m, 12H), 1.5–1.2 (m, 108H), 0.87 (m, 18H) ppm;

UV/Vis ($CH_2Cl_2$): $\lambda_{max}$ (ε)=574 (51 500), 535 (32 500), 445 nm (16 400) ($mol^{-1}$ $dm^3$ $cm^{-1}$).

Example 4

N,N'-Di(3,4,5-tridodecyloxyphenyl)-1,6,7,12-tetra(4-tert-butyl-phenoxy)perylene-3,4:9,10-tetracarboxylic diimide Example 1 was repeated, except that 0.25 g (0.25 mmol) of 1,6,7,12-tetra(4-tert-butylphenoxy)perylene-3,4:9,10-tetra-carboxylic dianhydride, 0.48 g (0.75 mmol) of 3,4,5-tridodecyloxyaniline, 0.04 g (0.2 mmol) of zinc acetate and 10 ml of quinoline were used.

This provided 0.52 g of a 98% pure product, which corresponds to a yield of 92%.

Analytical Data

Elemental analysis for $C_{148}H_{210}N_2O_{14}$ (2241.3) (% by weight calc./obs.):

C: 79.31/78.91; H: 9.44/9.27; N: 1.25/1.27;

1H NMR (200 MHz, $CDCl_3$, 25° C., TMS): δ=8.23 (s, 4H; H2,5,8,11), 7.24 (d, 3J (H,H)=8.7 Hz, 8H; H3'), 6.86 (d, 3J (H,H)=8.7 Hz, 8H; H2'), 6.41 (s, 4H; ArH), 3.98 (t, 4H; $OCH_2$), 3.89 (t, 8H; $OCH_2$), 1.75 (m, 12H), 1.6–1.2 (m, 108H), 1.26 (s, 36H; tert.Bu), 0.87 (m, 18H) ppm;

UV/Vis ($CH_2Cl_2$): $\lambda_{max}$ (ε)=580 (42 500), 542 (28 000), 452 nm (15 800 $mol^{-1}$ $dm^3$ $cm^{-1}$)

B) Investigation of the Properties of the Perylimides Prepared

Example 5
Characterization of the Liquid-crystalline Properties of the Perylimide of Example 1

A sample of the compound was heated to above the clear point of 376° C. and then cooled down slowly. Under a polarizing microscope, the formation of a spherulitic texture typical of columnar mesophases was observed with large pseudoisotropic regions, using crossed polarizers. Although the sample became glassy at lower temperatures, no further phase transition was detectable under the polarizing microscope or else by DSC (heating/cooling rate: 10° C./min). On renewed heating, the texture remained intact up to the clear point regardless of the heating rate.

The wide angle X-ray diffractogram (WAXS; Cu—Kα, Ni-filtered) of a sample cooled to room temperature exhibited a sharp reflex at 2θ=3.14° and a diffuse halo at 2θ=20°. An additional diffraction experiment on an oriented sample showed a hexagonal arrangement of the first order reflexes and thus suggested a disordered hexagonal discotic mesophase $D_{hd}$ having a lattice constant of 32.5 Å and one molecule per column segment.

Example 6
Characterization of the Liquid-crystalline Properties of the Perylimide of Example 4

A sample of the compound was heated to above the clear point of 346° C. and then cooled down slowly. Under a polarizing microscope, the formation of a spherulitic texture typical of columnar mesophases was observed with large pseudoisotropic regions, using crossed polarizers. Although the sample became glassy at lower temperatures, no further phase transition was detectable under the polarizing microscope or else by DSC (heating/cooling rate: 10° C./min). On renewed heating, the texture remained intact up to the clear point regardless of the heating rate.

The wide angle X-ray diffractogram (WAXS; Cu—Kα, Ni-filtered) of a sample cooled to room temperature exhibited two sharp reflexes at 2θ=3.57° and 2θ=6.12° and a diffuse halo at 2θ=20° suggesting a disordered hexagonal discotic mesophase $D_{hd}$ having a lattice constant of 28.7 Å and one molecule per column segment.

Example 7
Characterization of the Fluorescence Properties of the Perylimide of Example 4

Intensive fluorescence with a peak emission at 616 nm was observed in dichloromethane. The fluorescence quantum yield determined for an 8·10⁷ molar solution was 21%.

In aliphatic solvents such as methylcyclohexane, substantial aggregation was observed at high concentrations not only in the absorption but also in the emission spectra. The absorption maximum shifted to longer wavelengths by 19 nm and the emission maximum by 40 nm, which is believed to be due to excitonic interactions of the aggregated chromophores (J-aggregate). Nonetheless, an almost linear dependence on the concentration was observed for the intensity of fluorescence.

The fluorescence spectrum of a film of the compound deposited on quartz glass was almost identical with those obtained for concentrated solutions and similarly showed a red color with intensive fluorescence.

We claim:
1. A perylene-3,4:9,10-tetracarboxylic diimide of the formula I

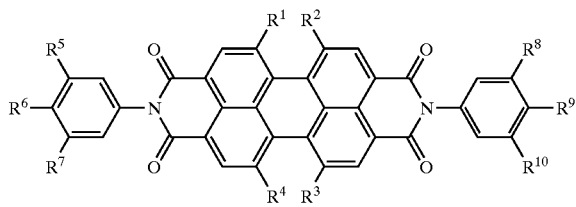

where
 $R^1$, $R^2$, $R^3$ and $R^4$ are independently hydrogen, chlorine, bromine or substituted or unsubstituted aryloxy, arylthio, arylamino, hetaryloxy or hetarylthio;
 $R^5$, $R^6$, $R^7$ $R^8$, $R^9$ and $R^{10}$ are independently hydrogen, or $C_{8-20}$-alkyl, $C_8$–$C_{20}$-alkoxy or $C_8$–$C_{20}$-alkylthio whose carbon chain may in each case contain up to four double bonds, with the proviso that at least four of these radicals are not hydrogen.

2. The perylene-3,4:9,10-tetracarboxylic diimide as claimed in claim 1 of formula I where
 $R^1$, $R^2$, $R^3$ and $R^4$ are independently hydrogen, chlorine, bromine or phenoxy which may be substituted by up to three of the following substituents: $C_1$–$C_{20}$-alkyl whose carbon chain may be interrupted by one or more moieties selected from the group consisting of —O—, —S—, —NR$^{11}$—, —CO— and —SO$_2$— and/or which may be substituted by one or more substituents selected from the group consisting of —COOR$^{11}$, —SO$_3$R$^{11}$, hydroxyl, cyano, $C_1$–$C_6$-alkoxy, $C_5$–$C_8$-cycloalkyl and a 5- to 7-membered, nitrogen containing heterocyclic radical which is attached by a nitrogen atom and which may contain another heteroatom; $C_1$–$C_6$-alkoxy; cyano; hydroxyl; halogen; nitro, —COOR$^{11}$ or —SO$_3$R$^{11}$;
 $R^5$, $R^6$, $R^7$ $R^8$, $R^9$ and $R^{10}$ are independently $C_8$–$C_{20}$-alkyl, $C_8$–$C_{20}$-alkoxy or $C_8$–$C_{20}$-alkylthio whose carbon chain may in each case contain up to four double bonds; and
 $R^{11}$ is hydrogen or $C_1$–$C_6$-alkyl.

3. The perylene-3,4:9,10-tetracarboxylic diimide as claimed in claim 1 of formula I where
 $R^1$, $R^2$, $R^3$ and $R^4$ are independently hydrogen or phenoxy which may be monosubstituted by $C_1$–$C_8$-alkyl; and
 $R^5$, $R^6$, $R^7$ $R^8$, $R^9$ and $R^{10}$ are each $C_{10}$–$C_{14}$-alkyl.

4. A process for preparing a perylene-3,4:9,10-tetracarboxylic diimide of the formula I as set forth in claim 1, which comprises reacting a perylene-3,4:9,10-tetracarboxylic dianhydride of formula II

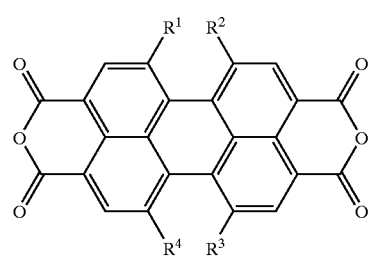

with identical or different primary amines of formulae III

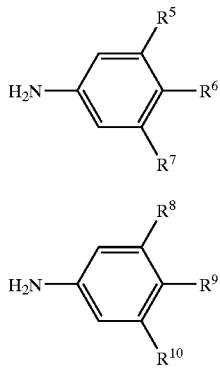

wherein R1–R10 are as defined in claim 1 in the presence of a polar aprotic solvent and of an imidation catalyst.

5. A process for preparing a perylene-3,4:9,10-tetracarboxylic diimide of claim 1 having the structure of formula Ia

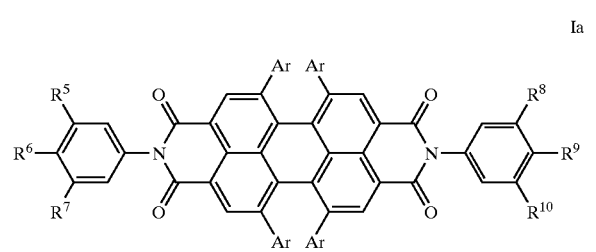

where Ar is substituted or unsubstituted aryloxy, arylthio, heteryloxy or hetarylthio and $R^5$–$R^6$ are as defined in claim 1, which comprises:

reacting 1,6,7,12-tetrachloroperylene-3,4:9,10-tetracarboxylic dianhydride (IIa) with identical or different primary amines of formulae III

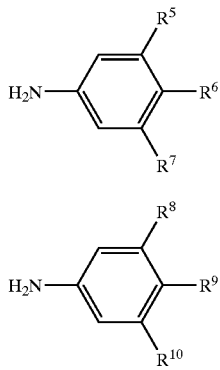

in the presence of a polar aprotic solvent and of an imidation catalyst; and reacting the resultant 1,6,7,12-tetrachloroperylene-3,4:9,10-tetracarboxylic diimide of formula I'

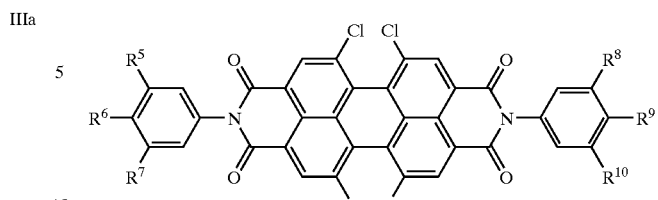

with an aromatic alcohol or thioalcohol of formula IV

in the presence of an inert aprotic solvent and of a non-nucleophilic or only minimally nucleophilic base.

6. A process for preparing a perylene-3,4:9,10-tetracarboxylic diimide of claim 1 having the structure of formula Ib

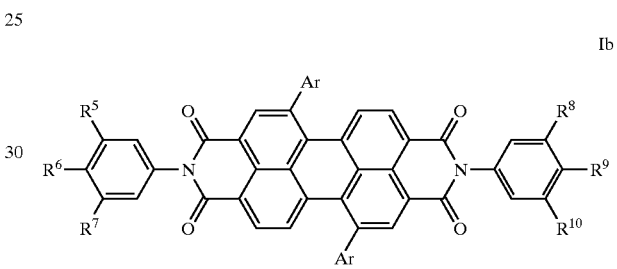

where Ar is substituted or unsubstituted aryloxy, arylthio, heteryloxy or hetarylthio and $R^5$–$R^6$ are as defined in claim 1, which comprises:

reacting 1,7-dibromoperylene-3,4:9,10-tetracarboxylic dianhydride (IIb) with identical or different primary amines of formulae III

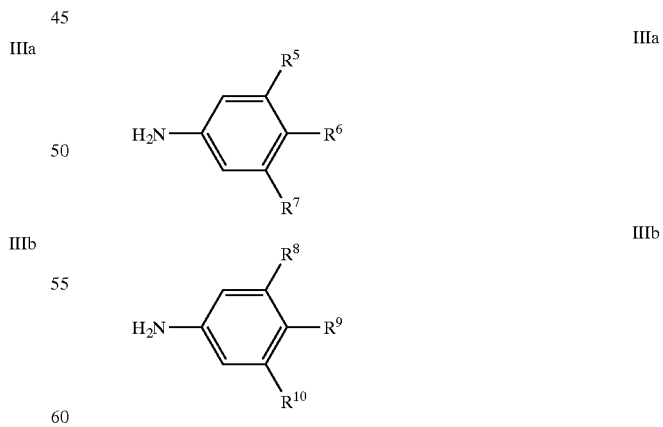

in the presence of a polar aprotic solvent and of an imidation catalyst; and reacting the resultant 1,7-dibromoperylene-3,4:9,10-tetracarboxylic diimide of formula I',

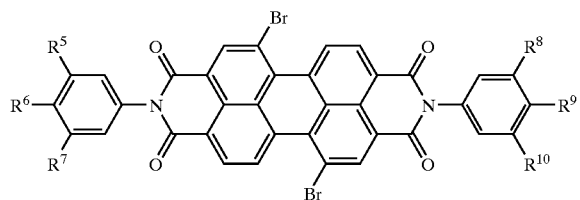

with an aromatic alcohol or thioalcohol of formula IV

H—Ar in the presence of an inert aprotic solvent and of a non-nucleophilic or only minimally nucleophilic base.

7. The perylene-3,4:9,10-tetracarboxylic diimide as claimed in claim 2 of formula I wherein said 5- to 7-membered nitrogen containing heterocyclic radical is morpholinyl, pyrrolidinyl or piperidyl.

8. The perylene-3,4:9,10-tetracarboxylic diimide as claimed in claim 2 wherein for groups $R^1$, $R^2$, $R^3$ and $R^4$; said aryloxy is phenoxy or 2-naphthyloxy, said arylthio is phenylthio or 2-naphthylthio, said arylamino is phenylamino, said hetaryloxy is 2-, 3- or 4-pyridyloxy or 2-, 4-, or 5-pyrimidyloxy and said hetarylthio is 2-, 3- or 4-pyridylthio or 2-, 4-, or 5-pyrimidylthio.

9. The process according to claim 4, wherein the primary amine III is reacted with said perylene-3,4:9,10-tetracarboxylic dianhydride in a molar ratio of 2:1 to 4:1.

10. The process according to claim 5, wherein the primary amine III is reacted with said perylene-3,4:9,10-tetracarboxylic dianhydride in a molar ratio of 2:1 to 4:1.

11. The process according to claim 6, wherein the primary amine III is reacted with said perylene-3,4:9,10-tetracarboxylic dianhydride in a molar ratio of 2:1 to 4:1.

12. The process according to claim 4, wherein the imidation catalyst is a Lewis acid salt of an organic or inorganic acid with a metal selected from the group consisting of zinc, iron, copper and magnesium or is an oxide of one of these metals.

13. The process according to claim 5, wherein the imidation catalyst is a Lewis acid salt of an organic or inorganic acid with a metal selected from the group consisting of zinc, iron, copper and magnesium or is an oxide of one of these metals.

14. The process according to claim 6, wherein the imidation catalyst is a Lewis acid salt of an organic or inorganic acid with a metal selected from the group consisting of zinc, iron, copper and magnesium or is an oxide of one of these metals.

* * * * *

UNITED STATES PATENT AND TRADEMARK OFFICE
CERTIFICATE OF CORRECTION

PATENT NO. : 6,806,368 B2
DATED : October 19, 2004
INVENTOR(S) : Würthner et al.

It is certified that error appears in the above-identified patent and that said Letters Patent is hereby corrected as shown below:

Title page, Item [54] and Column 1, line 1,
Title, should read -- LIQUID CRYSTALLINE 3,4:9,10-PERYLENETETRACARBOXYLIC ACID DIIMIDES --

Signed and Sealed this

Eighth Day of February, 2005

JON W. DUDAS
*Director of the United States Patent and Trademark Office*